US012734150B2

(12) United States Patent
Vannini et al.

(10) Patent No.: US 12,734,150 B2
(45) **Date of Patent: *Sep. 15, 2026**

(54) COMPOSITIONS AND METHODS FOR INCREASING T CELL FUNCTION

(71) Applicants: SOCIETE DES PRODUITS NESTLE S.A., Vevey (CH); LUDWIG INSTITUTE FOR CANCER RESEARCH LTD, Zurich (CH)

(72) Inventors: Nicola Vannini, La Croix (CH); George Coukos, Chexbres (CH); Serge Andre Dominique Rezzi, Semsales (CH); Julie Laval, Caux (FR); Caroline Monnard, Cheseaux-sur-Lausanne (CH); Marcela Rincon Restrepo, Lausanne (CH)

(73) Assignees: SOCIETE DES PRODUITS NESTLE S.A., Vevey (CH); LUDWIG INSTITUTE FOR CANCER RESEARCH LTD, Zurich (CH)

( * ) Notice: Subject to any disclaimer, the term of this patent is extended or adjusted under 35 U.S.C. 154(b) by 873 days.

This patent is subject to a terminal disclaimer.

(21) Appl. No.: 17/442,217

(22) PCT Filed: Mar. 27, 2020

(86) PCT No.: PCT/EP2020/058693

§ 371 (c)(1),
(2) Date: Sep. 23, 2021

(87) PCT Pub. No.: WO2020/201076

PCT Pub. Date: Oct. 8, 2020

(65) Prior Publication Data

US 2022/0168271 A1 Jun. 2, 2022

(30) Foreign Application Priority Data

Mar. 29, 2019 (EP) .................................... 19166183

(51) Int. Cl.

| | |
|---|---|
| ***A61K 31/37*** | (2006.01) |
| ***A61K 31/198*** | (2006.01) |
| ***A61K 31/706*** | (2006.01) |
| ***A61K 31/714*** | (2006.01) |
| ***A61K 40/11*** | (2025.01) |
| ***A61K 40/45*** | (2025.01) |
| ***C12N 5/0783*** | (2010.01) |

(52) U.S. Cl.

CPC ........... *A61K 31/37* (2013.01); *A61K 31/198* (2013.01); *A61K 31/706* (2013.01); *A61K 31/714* (2013.01); *A61K 40/11* (2025.01); *A61K 40/45* (2025.01); *C12N 5/0636* (2013.01); *A61K 2239/31* (2023.05); *A61K 2239/38* (2023.05); *C12N 2500/32* (2013.01); *C12N 2500/38* (2013.01); *C12N 2500/40* (2013.01)

(58) Field of Classification Search

CPC .............. A61K 31/714; A61K 39/4611; A61K 2239/31; A61P 35/00

See application file for complete search history.

(56) References Cited

U.S. PATENT DOCUMENTS

| | | | | |
|---|---|---|---|---|
| 2012/0251463 A1* | 10/2012 | Brenner | .................... A61P 3/06 424/48 |
| 2016/0348065 A1 | 12/2016 | Liu | |
| 2018/0362570 A1 | 12/2018 | Ganapati et al. | |

FOREIGN PATENT DOCUMENTS

| | | | |
|---|---|---|---|
| CN | 107412260 | 12/2017 | |
| CN | 107412260 A * | 12/2017 | ............. A61P 31/04 |
| CN | 108912342 | 11/2018 | |
| JP | 2000281571 | 10/2000 | |
| JP | 2017527572 A | 9/2017 | |
| JP | 2017533702 A | 11/2017 | |
| WO | 2012113835 | 8/2012 | |
| WO | 2017096246 | 6/2017 | |
| WO | 2017109195 A1 | 6/2017 | |
| WO | 2020166527 A1 | 8/2020 | |

OTHER PUBLICATIONS

Peking (CN107412260A; published on 2017; Machine translation).*

Japanese Office Action for Appl No. 2021-557008 dated Mar. 19, 2024.

Ma et al., "Serine is an Essential Metabolite for Effector T Cell Expansion", Cell Metabolism, vol. 25, Issue No. 2, Dec. 31, 2017, pp. 345-357.

Geiger et al., "L-Arginine Modulates T Cell Metabolism and Enhances Survival and Anti-tumor Activity", Cell, vol. 167, Issue No. 3, Dec. 30, 2016, pp. 1-14.

Tamura et al., "Immunomodulation by Vitamin B12: Augmentation of CD8+ T Lymphocytes and Natural Killer (NK) Cell Activity in Vitamin B12-Deficient Patients by Methyl-B12 Treatment", Clinical and Experimental Immunology, vol. 116, Issue No. 1, Dec. 31, 1999, pp. 28-32.

China Patent Office Communication for Application No. 202080023521.2, dated Nov. 10, 2022, 19 pages.

Totiger et al., "Urolithin A, A Novel Natural Compound to Target PI3K/AKT/mTOR Pathway in Pancreatic Cancer", Molecular Cancer Therapeutics, vol. 18, Issue No. 2, Nov. 7, 2018, pp. 301-311.

Japanese Office Action for Appl No. 2021-557008 dated Aug. 6, 2024, 4 pages.

European Office Action for Appl No. 20 713 030.3-1109 dated Dec. 19, 2024, 8 pages.

(Continued)

*Primary Examiner* — Pancham Bakshi
(74) *Attorney, Agent, or Firm* — K&L Gates LLP

(57) ABSTRACT

An agent for use in reducing T cell exhaustion and/or increasing T cell function, and/or boosting immunity, wherein the agent is selected from the group consisting of nicotinamide riboside, vitamin B12, a urolithin, manganese, serine, glycine, arginine, asparagine, and a combination of two or more thereof.

10 Claims, 4 Drawing Sheets

(56) References Cited

OTHER PUBLICATIONS

Japanese Office Action for Appl No. 2021-557008 dated Jan. 7, 2025, 4 pages.
Tao Z et al. Impact of T cell characteristics on CAR-T cell therapy in hematological malignancies. Blood Cancer J. Dec. 3, 2024;14(1):213. doi: 10.1038/s41408-024-01193-6.

* cited by examiner

A

B

C

COMPOSITIONS AND METHODS FOR INCREASING T CELL FUNCTION

CROSS REFERENCE TO RELATED APPLICATIONS

The present application is a National Stage of International Application No. PCT/EP2020/058693, filed on Mar. 27, 2020, which claims priority to European Patent Application No. 19166183.4, filed on Mar. 29, 2019, the entire contents of which are being incorporated herein by reference.

FIELD OF THE INVENTION

The present invention relates to agents and methods for use in immunotherapy. In particular, the invention relates to the use of agents such as nicotinamide riboside, vitamin B12, a urolithin, manganese, serine, glycine, arginine, asparagine, and combinations thereof, for increasing T cell function and reducing T cell exhaustion, for example as part of a method of adoptive T cell transfer.

BACKGROUND TO THE INVENTION

Immunotherapy is a highly effective and potentially curative systemic therapy for a number of diseases, including cancer. Melanoma, leukaemias and viral-associated malignancies are particularly responsive to this type of therapy, and successes in these fields have driven attempts to employ this approach against many cancer types.

Tumours produce biomolecules (tumour-associated antigens) that can be recognised by the immune system as abnormal and trigger an immune response. This may lead to the elimination of the cancer cells, however cancer cells utilise different strategies to escape the immune response and maintain an immunosuppressive microenvironment. Indeed, immunotherapies show various degrees of objective response rate when administered as a single therapy, for example from about 10-40% in metastatic melanoma treated with checkpoint blockade therapy. The reasons for the lack of response in certain patients are under investigation and are thought to be linked to a strongly immunosuppressive tumour microenvironment. The ability of the immune system to adequately respond to antigen presentation and activate itself is therefore key for the eradication of cancer cells, and is at the origin of the "immune fitness" concept that could be modulated by nutrition.

Activation of T cells is a regulated process that involves switches in energetic demands and energy production. Naïve T cells circulating in the blood or resting in secondary immune organs such as the spleen or the lymph nodes produce energy through fatty acid oxidation and oxidative phosphorylation metabolic pathways. However, once activated by antigen presentation, they turn anabolic and need to increase the rate of energy production to proliferate and fight the threat. As a result, the T cells switch their energy production to glycolysis when becoming effector T cells. After their proliferation and expansion cycle, effector T cells enter an exhaustion state, followed by cell death. However, a fraction of the effector T cells are able to expand their lifespan to turn into memory quiescent cells, which rest in secondary immune organs. These long-term T cells, which have lower energy demand, return to resting metabolism and therefore sustain their energy production through fatty acid oxidation and oxidative phosphorylation until they are activated again. Numerous studies have investigated the T cell metabolic switches and showed that the change from resting to activated, or activated to resting states is associated to the ability of those cells to modulate mitochondrial respiration through various biological mechanisms.

Although some studies have been carried out to probe the ability of certain agents to exert immunomodulatory effects by enhancing T cell function. There remains a significant need for solutions, such as nutritional interventions, that target optimisation of the immune system to improve therapeutic outcomes, for example in cancer and infection.

SUMMARY OF THE INVENTION

The inventors have identified a number of specific agents and combinations of agents that are capable of modulating immune cells. In particular, the inventors' studies have demonstrated a means of boosting the immune fitness of T cells after activation, which can be applied, for example, in adoptive cell therapy (e.g. in patients suffering from infections and cancer, as well as other immune deficiencies associated with T cell exhaustion).

The inventors have found that interventions with nicotinamide riboside, vitamin B12, urolithin A, manganese, serine, glycine, arginine, asparagine, and combinations thereof improve long-term T cell development.

Moreover, such interventions were tested during an adoptive cell transfer protocol and the inventors observed improvements in long-term T cell formation in an in vivo infectious model.

While not wishing to be bound by theory, it is believed that certain CD8 T cells, such as those infiltrating tumours, present an exhausted phenotype in the body and are not able to drive an effective immune response. The agents of the invention may be utilised to enhance T cell immune fitness, for example through reducing T cell exhaustion, before re-implantation into the patient.

Accordingly, in one aspect the invention provides an agent for use in reducing T cell exhaustion and/or increasing T cell function, and/or boosting immunity, wherein the agent is selected from the group consisting of nicotinamide riboside, vitamin B12, a urolithin, manganese, serine, glycine, arginine, asparagine, and a combination of two or more thereof.

In boosting immunity the agent(s) or combinations of agents disclosed herein may treat or prevent sub-optimal immunity in a subject, such a subject may be an immunocompromised subject.

Boosting immunity may refer to boosting tumour immunity in which case the subject may be a subject that has suffered from cancer for example a subject in remission or complete remission.

In another aspect, the invention provides an agent for use in the treatment of a bacterial or viral infection, wherein the agent is selected from the group consisting of nicotinamide riboside, vitamin B12, a urolithin, manganese, serine, glycine, arginine, asparagine, and a combination of two or more thereof.

In another aspect, the invention provides an agent for use in the prevention or treatment of cancer, wherein the agent is selected from the group consisting of nicotinamide riboside, vitamin B12, a urolithin, manganese, serine, glycine, arginine, asparagine, and a combination of two or more thereof.

Without wishing to be bound by theory, the inventors believe that the agents may be effective in the prevention of cancer by enhancing immune fitness, in particular of CD8-T cells, known to play a role in tumour immunity. The prevention may be with respect to recurrence of a cancer after remission.

In another aspect, the invention provides an agent for use in adoptive T cell transfer, wherein the agent is selected from the group consisting of nicotinamide riboside, vitamin B12, a urolithin, manganese, serine, glycine, arginine, asparagine, and a combination of two or more thereof.

In another aspect the invention provides nicotinamide riboside for use in reducing T cell exhaustion and/or increasing T cell function, and/or boosting immunity, preferably wherein the nicotinamide riboside is in combination with vitamin B12, a urolithin, manganese, serine, glycine, arginine and/or asparagine. In another aspect the invention provides nicotinamide riboside for use in the treatment of a bacterial or viral infection, preferably wherein the nicotinamide riboside is in combination with vitamin B12, a urolithin, manganese, serine, glycine, arginine and/or asparagine. In another aspect the invention provides nicotinamide riboside for use in the prevention or treatment of cancer, preferably wherein the nicotinamide riboside is in combination with vitamin B12, a urolithin, manganese, serine, glycine, arginine and/or asparagine. In another aspect the invention provides nicotinamide riboside for use in adoptive T cell transfer, preferably wherein the nicotinamide riboside is in combination with vitamin B12, a urolithin, manganese, serine, glycine, arginine and/or asparagine.

In another aspect the invention provides nicotinamide riboside for use in reducing T cell exhaustion and/or increasing T cell function, and/or boosting immunity, wherein the nicotinamide riboside is administered to a subject with vitamin B12, a urolithin, manganese, serine, glycine, arginine and/or asparagine. In another aspect the invention provides nicotinamide riboside for use in the treatment of a bacterial or viral infection, wherein the nicotinamide riboside is administered to a subject with vitamin B12, a urolithin, manganese, serine, glycine, arginine and/or asparagine. In another aspect the invention provides nicotinamide riboside for use in the prevention or treatment of cancer, wherein the nicotinamide riboside is administered to a subject with vitamin B12, a urolithin, manganese, serine, glycine, arginine and/or asparagine. In another aspect the invention provides nicotinamide riboside for use in adoptive T cell transfer, wherein the nicotinamide riboside is administered to a subject with vitamin B12, a urolithin, manganese, serine, glycine, arginine and/or asparagine.

In some embodiments, the nicotinamide riboside is administered to the subject simultaneously, sequentially or separately with vitamin B12, a urolithin, manganese, serine, glycine, arginine and/or asparagine, preferably simultaneously.

In another aspect the invention provides vitamin B12 for use in reducing T cell exhaustion and/or increasing T cell function, and/or boosting immunity, preferably wherein the vitamin B12 is in combination with nicotinamide riboside, a urolithin, manganese, serine, glycine, arginine and/or asparagine. In another aspect the invention provides vitamin B12 for use in the treatment of a bacterial or viral infection, preferably wherein the vitamin B12 is in combination with nicotinamide riboside, a urolithin, manganese, serine, glycine, arginine and/or asparagine. In another aspect the invention provides vitamin B12 for use in the prevention or treatment of cancer, preferably wherein the vitamin B12 is in combination with nicotinamide riboside, a urolithin, manganese, serine, glycine, arginine and/or asparagine. In another aspect the invention provides vitamin B12 for use in adoptive T cell transfer, preferably wherein the vitamin B12 is in combination with nicotinamide riboside, a urolithin, manganese, serine, glycine, arginine and/or asparagine.

In another aspect the invention provides vitamin B12 for use in reducing T cell exhaustion and/or increasing T cell function, and/or boosting immunity, wherein the vitamin B12 is administered to a subject with nicotinamide riboside, a urolithin, manganese, serine, glycine, arginine and/or asparagine. In another aspect the invention provides vitamin B12 for use in the treatment of a bacterial or viral infection, wherein the vitamin B12 is administered to a subject with nicotinamide riboside, a urolithin, manganese, serine, glycine, arginine and/or asparagine. In another aspect the invention provides vitamin B12 for use in the prevention or treatment of cancer, wherein the vitamin B12 is administered to a subject with nicotinamide riboside, a urolithin, manganese, serine, glycine, arginine and/or asparagine. In another aspect the invention provides vitamin B12 for use in adoptive T cell transfer, wherein the vitamin B12 is administered to a subject with nicotinamide riboside, a urolithin, manganese, serine, glycine, arginine and/or asparagine.

In some embodiments, the vitamin B12 is administered to the subject simultaneously, sequentially or separately with nicotinamide riboside, a urolithin, manganese, serine, glycine, arginine and/or asparagine, preferably simultaneously.

In another aspect the invention provides a urolithin for use in reducing T cell exhaustion and/or increasing T cell function, and/or boosting immunity, preferably wherein the urolithin is in combination with nicotinamide riboside, vitamin B12, manganese, serine, glycine, arginine and/or asparagine. In another aspect the invention provides a urolithin for use in the treatment of a bacterial or viral infection, preferably wherein the urolithin is in combination with nicotinamide riboside, vitamin B12, manganese, serine, glycine, arginine and/or asparagine. In another aspect the invention provides a urolithin for use in the prevention or treatment of cancer, preferably wherein the urolithin is in combination with nicotinamide riboside, vitamin B12, manganese, serine, glycine, arginine and/or asparagine. In another aspect the invention provides a urolithin for use in adoptive T cell transfer, preferably wherein the urolithin is in combination with nicotinamide riboside, vitamin B12, manganese, serine, glycine, arginine and/or asparagine.

In another aspect the invention provides a urolithin for use in reducing T cell exhaustion and/or increasing T cell function, and/or boosting immunity, wherein the urolithin is administered to a subject with nicotinamide riboside, vitamin B12, manganese, serine, glycine, arginine and/or asparagine. In another aspect the invention provides a urolithin for use in the treatment of a bacterial or viral infection, wherein the urolithin is administered to a subject with nicotinamide riboside, vitamin B12, manganese, serine, glycine, arginine and/or asparagine. In another aspect the invention provides a urolithin for use in the prevention or treatment of cancer, wherein the urolithin is administered to a subject with nicotinamide riboside, vitamin B12, manganese, serine, glycine, arginine and/or asparagine. In another aspect the invention provides a urolithin for use in adoptive T cell transfer, wherein the urolithin is administered to a subject with nicotinamide riboside, vitamin B12, manganese, serine, glycine, arginine and/or asparagine.

In some embodiments, the urolithin is administered to the subject simultaneously, sequentially or separately with nicotinamide riboside, vitamin B12, manganese, serine, glycine, arginine and/or asparagine, preferably simultaneously.

In another aspect the invention provides manganese for use in reducing T cell exhaustion and/or increasing T cell function, and/or boosting immunity, preferably wherein the manganese is in combination with nicotinamide riboside, vitamin B12, a urolithin, serine, glycine, arginine and/or asparagine. In another aspect the invention provides manganese for use in the treatment of a bacterial or viral infection, preferably wherein the manganese is in combination with nicotinamide riboside, vitamin B12, a urolithin, serine, glycine, arginine and/or asparagine. In another aspect the invention provides manganese for use in the prevention or treatment of cancer, preferably wherein the manganese is in combination with nicotinamide riboside, vitamin B12, a urolithin, serine, glycine, arginine and/or asparagine. In another aspect the invention provides manganese for use in adoptive T cell transfer, preferably wherein the manganese is in combination with nicotinamide riboside, vitamin B12, a urolithin, serine, glycine, arginine and/or asparagine.

In another aspect the invention provides manganese for use in reducing T cell exhaustion and/or increasing T cell function, and/or boosting immunity, wherein the manganese is administered to a subject with nicotinamide riboside, vitamin B12, a urolithin, serine, glycine, arginine and/or asparagine. In another aspect the invention provides manganese for use in the treatment of a bacterial or viral infection, wherein the manganese is administered to a subject with nicotinamide riboside, vitamin B12, a urolithin, serine, glycine, arginine and/or asparagine. In another aspect the invention provides manganese for use in the prevention or treatment of cancer, wherein the manganese is administered to a subject with nicotinamide riboside, vitamin B12, a urolithin, serine, glycine, arginine and/or asparagine. In another aspect the invention provides manganese for use in adoptive T cell transfer, wherein the manganese is administered to a subject with nicotinamide riboside, vitamin B12, a urolithin, serine, glycine, arginine and/or asparagine.

In some embodiments, the manganese is administered to the subject simultaneously, sequentially or separately with nicotinamide riboside, vitamin B12, a urolithin, serine, glycine, arginine and/or asparagine, preferably simultaneously.

In another aspect the invention provides serine for use in reducing T cell exhaustion and/or increasing T cell function, and/or boosting immunity, preferably wherein the serine is in combination with nicotinamide riboside, vitamin B12, a urolithin, manganese, glycine, arginine and/or asparagine. In another aspect the invention provides serine for use in the treatment of a bacterial or viral infection, preferably wherein the serine is in combination with nicotinamide riboside, vitamin B12, a urolithin, manganese, glycine, arginine and/or asparagine. In another aspect the invention provides serine for use in the prevention or treatment of cancer, preferably wherein the serine is in combination with nicotinamide riboside, vitamin B12, a urolithin, manganese, glycine, arginine and/or asparagine. In another aspect the invention provides serine for use in adoptive T cell transfer, preferably wherein the serine is in combination with nicotinamide riboside, vitamin B12, a urolithin, manganese, glycine, arginine and/or asparagine.

In another aspect the invention provides serine for use in reducing T cell exhaustion and/or increasing T cell function, and/or boosting immunity, wherein the serine is administered to a subject with nicotinamide riboside, vitamin B12, a urolithin, manganese, glycine, arginine and/or asparagine. In another aspect the invention provides serine for use in the treatment of a bacterial or viral infection, wherein the serine is administered to a subject with nicotinamide riboside, vitamin B12, a urolithin, manganese, glycine, arginine and/or asparagine. In another aspect the invention provides serine for use in the prevention or treatment of cancer, wherein the serine is administered to a subject with nicotinamide riboside, vitamin B12, a urolithin, manganese, glycine, arginine and/or asparagine. In another aspect the invention provides serine for use in adoptive T cell transfer, wherein the serine is administered to a subject with nicotinamide riboside, vitamin B12, a urolithin, manganese, glycine, arginine and/or asparagine.

In some embodiments, the serine is administered to the subject simultaneously, sequentially or separately with nicotinamide riboside, vitamin B12, a urolithin, manganese, glycine, arginine and/or asparagine, preferably simultaneously.

In another aspect the invention provides glycine for use in reducing T cell exhaustion and/or increasing T cell function, and/or boosting immunity, preferably wherein the glycine is in combination with nicotinamide riboside, vitamin B12, a urolithin, manganese, serine, arginine and/or asparagine. In another aspect the invention provides glycine for use in the treatment of a bacterial or viral infection, preferably wherein the glycine is in combination with nicotinamide riboside, vitamin B12, a urolithin, manganese, serine, arginine and/or asparagine. In another aspect the invention provides glycine for use in the prevention or treatment of cancer, preferably wherein the glycine is in combination with nicotinamide riboside, vitamin B12, a urolithin, manganese, serine, arginine and/or asparagine. In another aspect the invention provides glycine for use in adoptive T cell transfer, preferably wherein the glycine is in combination with nicotinamide riboside, vitamin B12, a urolithin, manganese, serine, arginine and/or asparagine.

In another aspect the invention provides glycine for use in reducing T cell exhaustion and/or increasing T cell function, and/or boosting immunity, wherein the glycine is administered to a subject with nicotinamide riboside, vitamin B12, a urolithin, manganese, serine, arginine and/or asparagine. In another aspect the invention provides glycine for use in the treatment of a bacterial or viral infection, wherein the glycine is administered to a subject with nicotinamide riboside, vitamin B12, a urolithin, manganese, serine, arginine and/or asparagine. In another aspect the invention provides glycine for use in the prevention or treatment of cancer, wherein the glycine is administered to a subject with nicotinamide riboside, vitamin B12, a urolithin, manganese, serine, arginine and/or asparagine. In another aspect the invention provides glycine for use in adoptive T cell transfer, wherein the glycine is administered to a subject with nicotinamide riboside, vitamin B12, a urolithin, manganese, serine, arginine and/or asparagine.

In some embodiments, the glycine is administered to the subject simultaneously, sequentially or separately with nicotinamide riboside, vitamin B12, a urolithin, manganese, serine, arginine and/or asparagine, preferably simultaneously.

In another aspect the invention provides arginine for use in reducing T cell exhaustion and/or increasing T cell function, and/or boosting immunity, preferably wherein the arginine is in combination with nicotinamide riboside, vitamin B12, a urolithin, manganese, serine, glycine and/or asparagine. In another aspect the invention provides arginine for use in the treatment of a bacterial or viral infection, preferably wherein the arginine is in combination with nicotinamide riboside, vitamin B12, a urolithin, manganese, serine, glycine and/or asparagine. In another aspect the invention provides arginine for use in the prevention or treatment of cancer, preferably wherein the arginine is in combination with nicotinamide riboside, vitamin B12, a urolithin, manganese, serine, glycine and/or asparagine. In another aspect the invention provides arginine for use in adoptive T cell transfer, preferably wherein the arginine is in combination with nicotinamide riboside, vitamin B12, a urolithin, manganese, serine, glycine and/or asparagine.

In another aspect the invention provides arginine for use in reducing T cell exhaustion and/or increasing T cell function, and/or boosting immunity, wherein the arginine is administered to a subject with nicotinamide riboside, vitamin B12, a urolithin, manganese, serine, glycine and/or asparagine. In another aspect the invention provides arginine for use in the treatment of a bacterial or viral infection, wherein the arginine is administered to a subject with nicotinamide riboside, vitamin B12, a urolithin, manganese, serine, glycine and/or asparagine. In another aspect the invention provides arginine for use in the prevention or treatment of cancer, wherein the arginine is administered to a subject with nicotinamide riboside, vitamin B12, a urolithin, manganese, serine, glycine and/or asparagine. In another aspect the invention provides arginine for use in adoptive T cell transfer, wherein the arginine is administered to a subject with nicotinamide riboside, vitamin B12, a urolithin, manganese, serine, glycine and/or asparagine.

In some embodiments, the arginine is administered to the subject simultaneously, sequentially or separately with nicotinamide riboside, vitamin B12, a urolithin, manganese, serine, glycine and/or asparagine, preferably simultaneously.

In another aspect the invention provides asparagine for use in reducing T cell exhaustion and/or increasing T cell function, and/or boosting immunity, preferably wherein the asparagine is in combination with nicotinamide riboside, vitamin B12, a urolithin, manganese, serine, glycine and/or arginine. In another aspect the invention provides asparagine for use in the treatment of a bacterial or viral infection, preferably wherein the asparagine is in combination with nicotinamide riboside, vitamin B12, a urolithin, manganese, serine, glycine and/or arginine. In another aspect the invention provides asparagine for use in the prevention or treatment of cancer, preferably wherein the asparagine is in combination with nicotinamide riboside, vitamin B12, a urolithin, manganese, serine, glycine and/or arginine. In another aspect the invention provides asparagine for use in adoptive T cell transfer, preferably wherein the asparagine is in combination with nicotinamide riboside, vitamin B12, a urolithin, manganese, serine, glycine and/or arginine.

In another aspect the invention provides asparagine for use in reducing T cell exhaustion and/or increasing T cell function, and/or boosting immunity, wherein the asparagine is administered to a subject with nicotinamide riboside, vitamin B12, a urolithin, manganese, serine, glycine and/or arginine. In another aspect the invention provides asparagine for use in the treatment of a bacterial or viral infection, wherein the asparagine is administered to a subject with nicotinamide riboside, vitamin B12, a urolithin, manganese, serine, glycine and/or arginine. In another aspect the invention provides asparagine for use in the prevention or treatment of cancer, wherein the asparagine is administered to a subject with nicotinamide riboside, vitamin B12, a urolithin, manganese, serine, glycine and/or arginine. In another aspect the invention provides asparagine for use in adoptive T cell transfer, wherein the asparagine is administered to a subject with nicotinamide riboside, vitamin B12, a urolithin, manganese, serine, glycine and/or arginine.

In some embodiments, the asparagine is administered to the subject simultaneously, sequentially or separately with nicotinamide riboside, vitamin B12, a urolithin, manganese, serine, glycine and/or arginine, preferably simultaneously.

In another aspect, the invention provides a combination of two or more agents selected from the group consisting of (a) nicotinamide riboside; (b) vitamin B12; (c) a urolithin; (d) manganese; (e) serine; (f) glycine; (g) arginine; and (h) asparagine for use in reducing T cell exhaustion and/or increasing T cell function and/or boosting immunity. A particularly effective combination of agents may be nicotinamide riboside, vitamin B12, a urolithin and manganese.

In some embodiments, two or more of (a)-(h) are administered to a subject simultaneously, sequentially or separately. In preferred embodiments, two or more of (a)-(h) are administered to a subject simultaneously. In even more preferred embodiments (a), (b), (c) and (d) are administered to a subject simultaneously.

In another aspect, the invention provides a composition comprising one or more agents selected from the group consisting of nicotinamide riboside, vitamin B12, a urolithin, manganese, serine, glycine, arginine and asparagine for use in reducing T cell exhaustion and/or increasing T cell function and/or boosting immunity. In a preferred embodiment said composition comprises nicotinamide riboside, vitamin B12, a urolithin and manganese.

In another aspect, the invention provides a method for reducing T cell exhaustion and/or increasing T cell function, and/or boosting immunity, wherein the method comprises administering one or more agents selected from the group consisting of nicotinamide riboside, vitamin B12, a urolithin, manganese, serine, glycine, arginine and asparagine to a subject in need thereof. In a preferred embodiment the agent administered in said method is a combination of nicotinamide riboside, vitamin B12, a urolithin and manganese.

The combination of nicotinamide riboside, vitamin B12, a urolithin and manganese may be particularly effective.

In another aspect, the invention provides a combination of two or more agents selected from the group consisting of (a) nicotinamide riboside; (b) vitamin B12; (c) a urolithin; (d) manganese; (e) serine; (f) glycine; (g) arginine; and (h) asparagine for use in the treatment of a bacterial or viral infection. A particularly effective combination of agents may be nicotinamide riboside, vitamin B12, a urolithin and manganese.

In some embodiments, two or more of (a)-(h) are administered to a subject simultaneously, sequentially or separately. In preferred embodiments, two or more of (a)-(h) are administered to a subject simultaneously. In even more preferred embodiments (a), (b), (c) and (d) are administered to a subject simultaneously.

In another aspect, the invention provides a composition comprising one or more agents selected from the group consisting of nicotinamide riboside, vitamin B12, a urolithin, manganese, serine, glycine, arginine and asparagine for use in the treatment of a bacterial or viral infection. In a preferred embodiment said composition comprises nicotinamide riboside, vitamin B12, a urolithin and manganese.

In another aspect, the invention provides a method for the treatment of a bacterial or viral infection, wherein the method comprises administering one or more agents selected from the group consisting of nicotinamide riboside, vitamin B12, a urolithin, manganese, serine, glycine, arginine and asparagine to a subject in need thereof. In a preferred embodiment the agent administered in said method is a combination of nicotinamide riboside, vitamin B12, a urolithin and manganese.

In another aspect, the invention provides a combination of two or more agents selected from the group consisting of (a) nicotinamide riboside; (b) vitamin B12; (c) a urolithin; (d)

manganese; (e) serine; (f) glycine; (g) arginine; and (h) asparagine for use in the prevention or treatment of cancer. A particularly effective combination of agents may be nicotinamide riboside, vitamin B12, a urolithin and manganese.

In some embodiments, two or more of (a)-(h) are administered to a subject simultaneously, sequentially or separately. In preferred embodiments, two or more of (a)-(h) are administered to a subject simultaneously. In even more preferred embodiments (a), (b), (c) and (d) are administered to a subject simultaneously.

In another aspect, the invention provides a composition comprising one or more agents selected from the group consisting of nicotinamide riboside, vitamin B12, a urolithin, manganese, serine, glycine, arginine and asparagine for use in the prevention or treatment of cancer. In a preferred embodiment said composition comprises nicotinamide riboside, vitamin B12, a urolithin and manganese.

In another aspect, the invention provides a method for the prevention or treatment of cancer, wherein the method comprises administering one or more agents selected from the group consisting of nicotinamide riboside, vitamin B12, a urolithin, manganese, serine, glycine, arginine and asparagine to a subject in need thereof. In a preferred embodiment the agent administered in said method is a combination of nicotinamide riboside, vitamin B12, a urolithin and manganese.

In another aspect, the invention provides a combination of two or more agents selected from the group consisting of (a) nicotinamide riboside; (b) vitamin B12; (c) a urolithin; (d) manganese; (e) serine; (f) glycine; (g) arginine; and (h) asparagine for use in adoptive T cell transfer. A particularly effective combination of agents may be nicotinamide riboside, vitamin B12, a urolithin and manganese In some embodiments, two or more of (a)-(h) are administered to a subject simultaneously, sequentially or separately. In preferred embodiments, two or more of (a)-(h) are administered to a subject simultaneously. In even more preferred embodiments (a), (b), (c) and (d) are administered to a subject simultaneously.

In another aspect, the invention provides a composition comprising one or more agents selected from the group consisting of nicotinamide riboside, vitamin B12, a urolithin, manganese, serine, glycine, arginine and asparagine for use in adoptive T cell transfer. In a preferred embodiment said composition comprises nicotinamide riboside, vitamin B12, a urolithin and manganese.

In another aspect, the invention provides a method for adoptive T cell transfer, wherein the method comprises administering one or more agents selected from the group consisting of nicotinamide riboside, vitamin B12, a urolithin, manganese, serine, glycine, arginine and asparagine to a subject in need thereof. In a preferred embodiment the agent administered in said method is a combination of nicotinamide riboside, vitamin B12, a urolithin and manganese.

In some embodiments, the agent is used as part of a method of adoptive T cell transfer.

In another aspect, the invention provides use of an agent selected from the group consisting of nicotinamide riboside, vitamin B12, a urolithin, manganese, serine, glycine, arginine, asparagine, and a combination of two or more thereof, for reducing T cell exhaustion and/or increasing T cell function in a population of T cells. A particularly effective combination of agents may be nicotinamide riboside, vitamin B12, a urolithin and manganese.

In some embodiments, the use is in vitro use or ex vivo use.

In another aspect, the invention provides in vitro use of an agent selected from the group consisting of nicotinamide riboside, vitamin B12, a urolithin, manganese, serine, glycine, arginine, asparagine, and a combination of two or more thereof, for reducing T cell exhaustion and/or increasing T cell function in a population of T cells. A particularly effective combination of agents may be nicotinamide riboside, vitamin B12, a urolithin and manganese.

In some embodiments, the T cell function is T cell memory function.

In some embodiments, the use increases T cell levels in a subject.

In some embodiments, the agent is nicotinamide riboside, or a combination comprising nicotinamide riboside. In some embodiments, the agent is vitamin B12, or a combination comprising vitamin B12.

In preferred embodiments, the combination is nicotinamide riboside, a urolithin and manganese. In preferred embodiments, the combination is nicotinamide riboside, vitamin B12 and manganese. In preferred embodiments, the combination is nicotinamide riboside, a urolithin and vitamin B12. In preferred embodiments, the combination is serine, glycine and vitamin B12. In preferred embodiments, the combination is a urolithin, vitamin B12 and manganese.

A particularly effective combination of agents may be nicotinamide riboside, vitamin B12, a urolithin and manganese. Accordingly, in preferred embodiments the combination is nicotinamide riboside, vitamin B12, a urolithin and manganese.

In any aspect or embodiment disclosed herein the urolithin may be urolithin A.

In preferred embodiments, the urolithin is urolithin A.

In some embodiments, the agent or combination is in the form of a composition.

In some embodiments, the agent or combination is in the form of a pharmaceutical or nutritional composition, preferably a nutritional composition.

In some embodiments, the agent or combination is in the form of a tablet, gel capsule, powder, milk powder, food product, liquid format (e.g. ready to drink format) and/or beverage.

In some embodiments, the agent or combination is in the form of a food product, food supplement, nutraceutical, food for special medical purpose (FSMP), nutritional supplement, dairy-based drink, low-volume liquid supplement or meal replacement beverage.

In preferred embodiments, a subject is a human.

In some embodiments, a subject is an immunocompromised subject.

In some embodiments, a subject has undergone an intervention selected from the group consisting of chemotherapy; radiotherapy; and surgery.

In another aspect, the invention provides a method for expanding a population of T cells comprising contacting the population of T cells with an agent selected from the group consisting of nicotinamide riboside, vitamin B12, a urolithin, manganese, serine, glycine, arginine, asparagine, and a combination of two or more thereof. In a preferred embodiment the agent administered in said method is a combination of nicotinamide riboside, vitamin B12, a urolithin and manganese.

In another aspect, the invention provides a population of T cells obtainable by a method of the invention.

In another aspect, the invention provides a composition for reducing T cell exhaustion and/or increasing T cell function and/or boosting immunity, comprising: (a) nicotinamide riboside, a urolithin and manganese; (b) nicotinamide riboside, vitamin B12 and manganese; (c) nicotinamide riboside, a urolithin and vitamin B12; (d) serine, glycine and vitamin B12; or (e) a urolithin, vitamin B12 and manganese. In a preferred embodiment said composition comprises nicotinamide riboside, vitamin B12, a urolithin and manganese.

In another aspect, the invention provides composition for use in reducing T cell exhaustion and/or increasing T cell function and/or boosting immunity, in a subject, wherein the composition comprises an agent or combination as defined in any preceding claim.

In another aspect, the invention provides a composition for the treatment of a bacterial or viral infection comprising: (a) nicotinamide riboside, a urolithin and manganese; (b) nicotinamide riboside, vitamin B12 and manganese; (c) nicotinamide riboside, a urolithin and vitamin B12; (d) serine, glycine and vitamin B12; or (e) a urolithin, vitamin B12 and manganese. In a preferred embodiment said composition comprises nicotinamide riboside, vitamin B12, a urolithin and manganese.

In another aspect, the invention provides composition for use in the treatment of a bacterial or viral infection in a subject, wherein the composition comprises an agent or combination as defined in any preceding claim.

In another aspect, the invention provides a composition for the prevention or treatment of cancer comprising: (a) nicotinamide riboside, a urolithin and manganese; (b) nicotinamide riboside, vitamin B12 and manganese; (c) nicotinamide riboside, a urolithin and vitamin B12; (d) serine, glycine and vitamin B12; or (e) a urolithin, vitamin B12 and manganese. In a preferred embodiment said composition comprises nicotinamide riboside, vitamin B12, a urolithin and manganese.

In another aspect, the invention provides composition for use in the prevention or treatment of cancer in a subject, wherein the composition comprises an agent or combination as defined in any preceding claim.

In another aspect, the invention provides composition for use in adoptive T cell transfer, wherein the composition comprises an agent or combination as defined in any preceding claim.

A method for reducing T cell exhaustion and/or increasing T cell function in a population of T cells comprising contacting the population of T cells with an agent selected from the group consisting of nicotinamide riboside, vitamin B12, a urolithin, manganese, serine, glycine, arginine, asparagine, and a combination of two or more thereof. In a preferred embodiment the agent administered in said method is a combination of nicotinamide riboside, vitamin B12, a urolithin and manganese.

In some embodiments, the method is an in vitro or ex vivo method.

A method of engrafting a subject with T cells a population of T cells with an agent selected from the group consisting of nicotinamide riboside, vitamin B12, a urolithin, manganese, serine, glycine, arginine, asparagine, and a combination of two or more thereof, and administering the population of T cells to a subject. In a preferred embodiment the agent administered in said method is a combination of nicotinamide riboside, vitamin B12, a urolithin and manganese.

A method for treatment of a bacterial or viral infection comprising contacting a population of T cells with an agent selected from the group consisting of nicotinamide riboside, vitamin B12, a urolithin, manganese, serine, glycine, arginine, asparagine, and a combination of two or more thereof, and administering the population of T cells to a subject. In a preferred embodiment the agent administered in said method is a combination of nicotinamide riboside, vitamin B12, a urolithin and manganese.

A method for prevention or treatment of cancer comprising contacting a population of T cells with an agent selected from the group consisting of nicotinamide riboside, vitamin B12, a urolithin, manganese, serine, glycine, arginine, asparagine, and a combination of two or more thereof, and administering the population of T cells to a subject. In a preferred embodiment the agent administered in said method is a combination of nicotinamide riboside, vitamin B12, a urolithin and manganese.

A method for adoptive T cell transfer comprising contacting a population of T cells with an agent selected from the group consisting of nicotinamide riboside, vitamin B12, a urolithin, manganese, serine, glycine, arginine, asparagine, and a combination of two or more thereof, and administering the population of T cells to a subject. In a preferred embodiment the agent administered in said method is a combination of nicotinamide riboside, vitamin B12, a urolithin and manganese.

Figure 1:
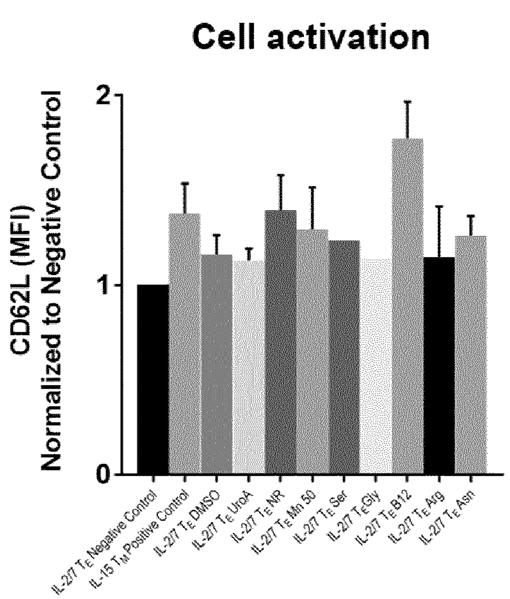
FIG. 1
Figure 1:
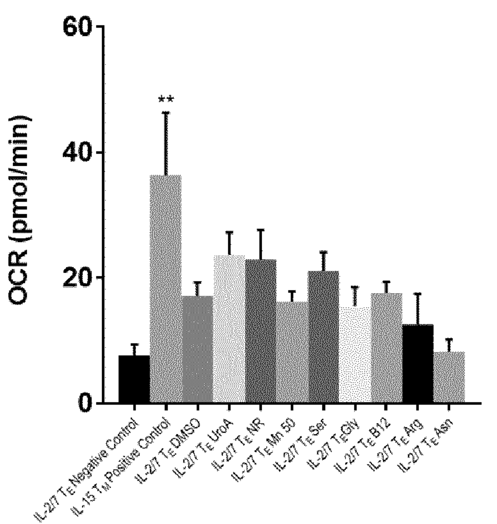
Figure 1:
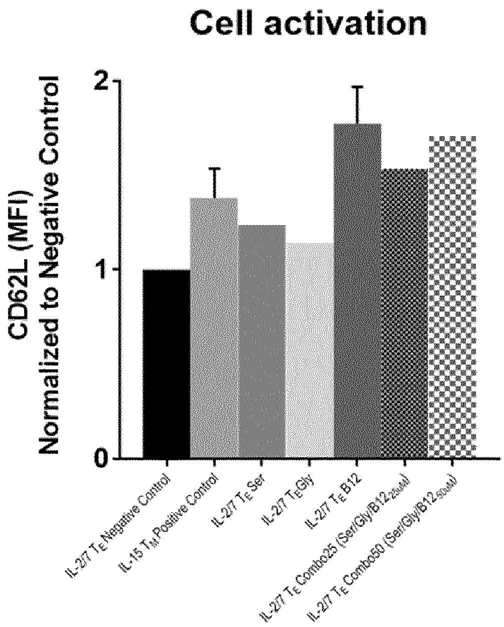
Figure 1:
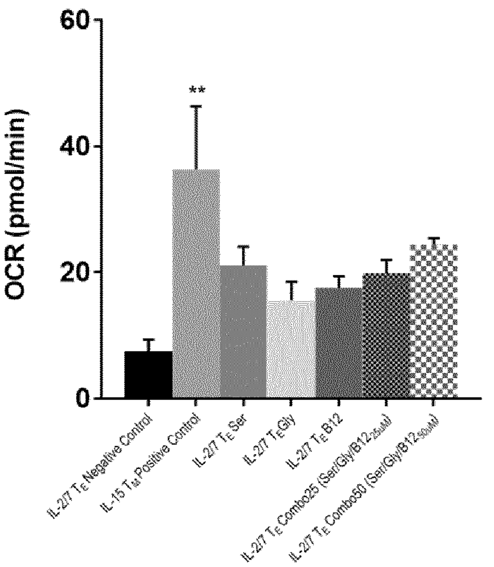
Figure 1:
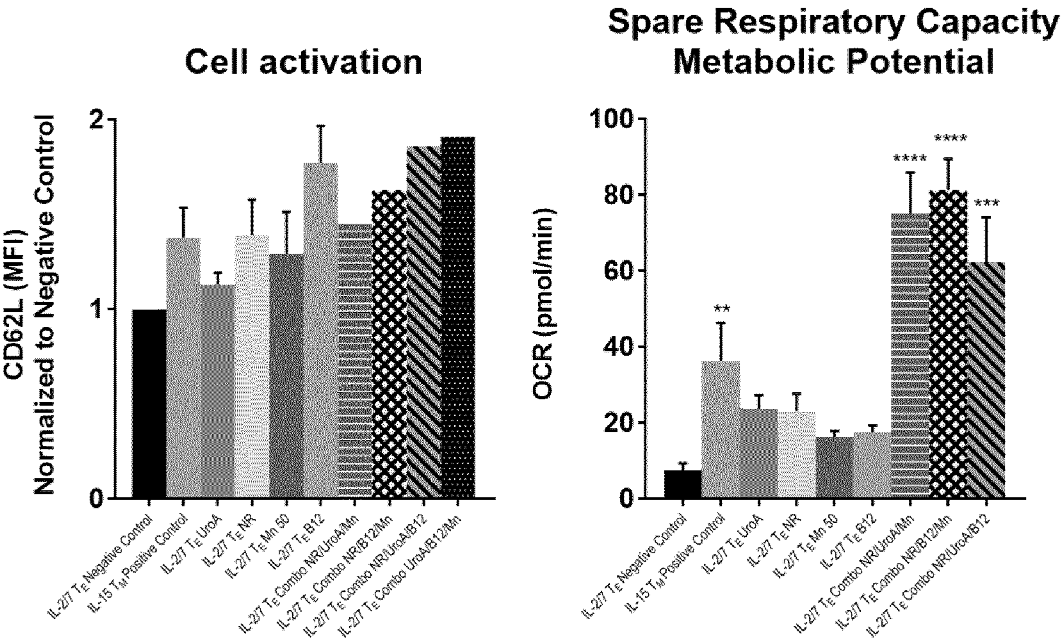

Agents and combinations thereof increase T cell function in vitro as determined by CD62L expression (left panels) and spare respiratory capacity (right panels). Results are shown for individual agents (A); combinations of serine, glycine and vitamin B12 (B); and a number of combinations of nicotinamide riboside (NR), urolithin A (UroA), manganese and vitamin B12 (C).

FIG. 2

Agents increase T cell function in vivo as determined by increased T cell levels in blood and spleen (A); increased MPEC levels in blood and spleen (B); increased memory T cell levels in blood and spleen (C); and increased CXCR3 expression and cytokine production (D).

DETAILED DESCRIPTION OF THE INVENTION

The terms “comprising”, “comprises” and “comprised of” as used herein are synonymous with “including” or “includes”; or “containing” or “contains”, and are inclusive or open-ended and do not exclude additional, non-recited members, elements or steps. The terms “comprising”, “comprises” and “comprised of” also include the term “consisting of”.

T Cell

T cells (also refer to as T lymphocytes) are a type of lymphocyte that play an important role in cell-mediated immunity. They can be distinguished from other lymphocytes, for example B cells and natural killer cells (NK cells), by the expression of the T cell receptor (TCR) on the surface of the cell.

Cytotoxic T cells ($T_C$ cells or CTLs; also referred to as killer T cells) destroy virally infected cells and tumour cells. They are also implicated in transplant rejection. $T_C$ cells express CD8 on their surface. These cells recognise targets by binding to antigens associated with MHC class I, which is present on the surface of all nucleated cells.

Helper T cells ($T_H$ cells) assist other white blood cells in immunologic processes, including maturation of B cells into plasma cells and memory B cells, and activation of cytotoxic T cells and macrophages. $T_H$ cells express CD4 on their surface. $T_H$ cells become activated when they are presented with peptide antigens by MHC class II molecules on the surface of antigen presenting cells (APCs). $T_H$ cells can differentiate into one of several subtypes, including $T_H1$, $T_H2$, $T_H3$, $T_H17$, Th9 or $T_{FH}$, which secrete different cytokines to facilitate different types of immune responses.

Regulatory T cells ($T_{reg}$ cells; formerly known as suppressor T cells), are crucial for the maintenance of immunological tolerance. Their major role is to shut down T cell-mediated immunity towards the end of an immune reaction and to suppress auto-reactive T cells that escaped the process of negative selection in the thymus.

Two major classes of $CD4^+$ $T_{reg}$ cells have been described: naturally occurring $T_{reg}$ cells and adaptive $T_{reg}$ cells.

Naturally occurring $T_{reg}$ cells ($CD4^+CD25^+FOXP3^+$ $T_{reg}$ cells) arise in the thymus and have been linked to interactions between developing T cells with both myeloid ($CD11c^+$) and plasmacytoid ($CD123^+$) dendritic cells that have been activated with TSLP. Naturally occurring $T_{reg}$ cells can be distinguished from other T cells by the presence of an intracellular molecule called FOXP3. Mutations of the FOXP3 gene can prevent regulatory T cell development, causing the fatal autoimmune disease IPEX.

Adaptive $T_{reg}$ cells (also known as Tr1 cells or Th3 cells) may originate during a normal immune response.

Effector T cells are the overall group of T cell types that actively and immediately respond to a stimulus. Effector T cells include helper, killer and regulatory T cells.

Memory T cells are the counterpart of effector cells, which are longer-lived to target future infections. Memory T cells persist long-term after an infection has resolved. They quickly expand to large numbers of effector T cells upon re-exposure to their cognate antigen, thus providing the immune system with "memory" against past infections. Memory T cells may be either $CD4^+$ or $CD8^+$ and typically express the cell surface protein CD45RO.

Memory T cells comprise three subtypes: central memory T cells ($T_{CM}$ cells); effector memory T cells ($T_{EM}$ cells); and T memory stem cells ($T_{MSC}$).

In preferred embodiments, the T cell contacted with an agent or combination of the invention is a $CD8^+$ T cell.

The invention also provides a T cell or population of T cells obtainable by the method of the invention.

The T cell for use in the invention may be isolated from a sample, such as a peripheral blood sample, from a subject or an unconnected donor. The T cell may be from a peripheral blood mononuclear cell (PBMC) sample. T cells may be activated and/or expanded prior to or simultaneously with being contacted with an agent of combination of the invention.

The population of T cells may be a population of tumour-infiltrating lymphocytes (TILs). TILs may be, for example, isolated from a tumour mass excised from a subject.

A T cell of the invention may be prepared by:

(a) isolating a T cell-containing sample from a subject or other source listed above, optionally enriching the sample for T cells or a type of T cell; and
(b) contacting the T cell with an agent or combination of the invention.

The T cells may then be purified.

The T cells of the invention may be, for example, human or murine T cells. Preferably the T cells are human T cells.

Although the disclosure herein may refer to a T cell, the invention also relates to populations of the T cells of the invention.

Isolation and Enrichment of Populations of Cells

Populations of cells, such as T cells, are disclosed herein. In some embodiments, the population of cells is an isolated population of cells.

The term "isolated population" as used herein refers to a population of cells that is not comprised within the body. An isolated population of cells may have been previously removed from a subject. An isolated population of cells may be cultured and manipulated ex vivo or in vitro using standard techniques known in the art. An isolated population of cells may later be reintroduced into a subject. Said subject may be the same subject from which the cells were originally isolated or a different subject.

A population of cells may be purified selectively for cells that exhibit a specific phenotype or characteristic, and from other cells which do not exhibit that phenotype or characteristic, or exhibit it to a lesser degree. For example, a population of cells that expresses a specific marker (such as CD8) may be purified from a starting population of cells. Alternatively, or in addition, a population of cells that does not express another marker may be purified.

The term "enriching" as used herein refers to an increase in the concentration of a type of cells within a population. The concentration of other types of cells may be concomitantly reduced.

Purification or enrichment may result in the population of cells being substantially pure of other types of cell.

Purifying or enriching for a population of cells expressing a specific marker (e.g. CD8) may be achieved by using an agent that binds to that marker, preferably substantially specifically to that marker.

An agent that binds to a cellular marker may be an antibody, for example an anti-CD8 antibody.

The term "antibody" as used herein refers to complete antibodies or antibody fragments capable of binding to a selected target, and including Fv, ScFv, F(ab') and $F(ab')_2$, monoclonal and polyclonal antibodies, engineered antibodies including chimeric, CDR-grafted and humanised antibodies, and artificially selected antibodies produced using phage display or alternative techniques.

In addition, alternatives to classical antibodies may also be used in the invention, for example "avibodies", "avimers", "anticalins", "nanobodies" and "DARPins".

The agents that bind to specific markers may be labelled so as to be identifiable using any of a number of techniques known in the art. The agent may be inherently labelled, or may be modified by conjugating a label thereto. By "conjugating" it is to be understood that the agent and label are operably linked. This means that the agent and label are linked together in a manner which enables both to carry out their function (e.g. binding to a marker, allowing fluorescent identification, or allowing separation when placed in a magnetic field) substantially unhindered. Suitable methods of conjugation are well known in the art and would be readily identifiable by the skilled person.

A label may allow, for example, the labelled agent and any cell to which it is bound to be purified from its environment (e.g. the agent may be labelled with a magnetic bead or an affinity tag, such as avidin), detected or both. Detectable markers suitable for use as a label include fluorophores (e.g. green, cherry, cyan and orange fluorescent proteins) and peptide tags (e.g. His tags, Myc tags, FLAG tags and HA tags).

A number of techniques for separating a population of cells expressing a specific marker are known in the art. These include magnetic bead-based separation technologies (e.g. closed-circuit magnetic bead-based separation), flow cytometry, fluorescence-activated cell sorting (FACS), affinity tag purification (e.g. using affinity columns or beads, such as biotin columns to separate avidin-labelled agents) and microscopy-based techniques.

It may also be possible to perform the separation using a combination of different techniques, such as a magnetic bead-based separation step followed by sorting of the resulting population of cells for one or more additional (positive or negative) markers by flow cytometry.

Clinical grade separation may be performed, for example, using the CliniMACS® system (Miltenyi). This is an example of a closed-circuit magnetic bead-based separation technology.

T Cell Function

Activation of T cells is a regulated process that involves switches in energetic demands and energy production. Naïve T cells circulating in the blood or resting in secondary immune organs such as the spleen or the lymph nodes produce energy through fatty acid oxidation and oxidative phosphorylation metabolic pathways. However, once activated by antigen presentation, they turn anabolic and need to increase the rate of energy production to proliferate and fight the threat. As a result, the T cells switch their energy production to glycolysis when becoming effector T cells. After their proliferation and expansion cycle, effector T cells enter an exhaustion state, followed by cell death. However, a fraction of the effector T cells are able to expand their lifespan to turn into memory quiescent cells, which rest in secondary immune organs. These long-term T cells, which have lower energy demand, return to resting metabolism and therefore sustain their energy production through fatty acid oxidation and oxidative phosphorylation until they are activated again.

The uses and methods of the invention provide reduction in T cell exhaustion in a population of T cells, for example a population of tumour-infiltrating lymphocytes (TILs).

T cell exhaustion may be characterised by increased expression of programmed cell death 1 (PD-1) and/or decreased cytokine production. Reduction in T cell exhaustion may prevent or reverse one or more such characteristics.

The uses and methods of the invention provide T cells that have increased T cell function, such as increased T cell memory function or T cell effector function, preferably T cell memory function.

The reduced T cell exhaustion and/or increased T cell function may increase immune fitness for example in ageing subjects or subjects with infection, inflammatory diseases and/or cancer.

In some embodiments, the T cell function comprises T cell effector function. In some embodiments, the T cell function is T cell effector function.

T cell effector function may correlate with the number of T cells in a population that express the surface marker CXCR3 and/or are able to produce cytokines, such as IFN$\alpha$ and TNF$\alpha$.

In some embodiments, the T cell function comprises T cell memory function. In some embodiments, the T cell function is T cell memory function.

The term “memory function” refers to a diverse array of behaviours acquired by antigen-experienced T cells that survive following an initial primary response; these include increased basal proliferation and survival in the absence of antigen, a lower threshold for activation following a subsequent antigen encounter and rapid responsiveness (in terms of proliferation, cytokine generation and cytotoxicity).

Memory function may correlate with spare respiratory capacity. Increased memory function in a population of T cells may be an increased spare respiratory capacity in a population of T cells after contact with an agent or combination of the invention compared to a population of T cells not contacted with an agent or combination of the invention, but under otherwise substantially identical conditions. The contact may be, for example, through contact in in vitro culture or contact through administration to a subject.

Spare respiratory capacity may be measured using methods known in the art, for example using the Seahorse assay (e.g. as disclosed herein in the Examples).

Memory function may correlate with the number of T cells in a population that express CD62L. Increased memory function in a population of T cells may be an increased percentage of T cells expressing CD62L in a population of T cells after contact with an agent or combination of the invention compared to a population of T cells not contacted with an agent or combination of the invention, but under otherwise substantially identical conditions. The contact may be, for example, through contact in in vitro culture or contact through administration to a subject.

Memory function may correlate with the number of memory precursor effector cells (MPECs) and/or memory cells in a population of T cells. MPECs may be characterised as $CD127^+$ and $KLRG1^-$. Memory T cells may be characterised as $CD27^+$ and $CD43^+$. Increased memory function in a population of cells may be an increased percentage of MPECs and/or memory T cells in a population of T cells after contact with an agent or combination of the invention compared to a population of T cells not contacted with an agent or combination of the invention, but under otherwise substantially identical conditions. The contact may be, for example, through contact in in vitro culture or contact through administration to a subject.

Memory function may be assessed using one or more of the above means.

In some embodiments, the increased T cell function is increased T cell persistence. Accordingly, in another aspect the invention provides an agent for use in increasing T cell persistence, wherein the agent is selected from the group consisting of nicotinamide riboside, vitamin B12, a urolithin, manganese, serine, glycine, arginine, asparagine, and a combination of two or more thereof. In another aspect, the invention provides use (e.g. in vitro use) of an agent selected from the group consisting of nicotinamide riboside, vitamin B12, a urolithin, manganese, serine, glycine, arginine, asparagine, and a combination of two or more thereof, for increasing persistence in a population of T cells.

The term “persistence” refers to the ability of the cells to survive long term in a recipient. In some embodiments, persistence is assessed at about 1-72 months, 1-48 months, 1-24 months or 1-12 months after transplantation. In other embodiments, persistence is assessed at about 1, 2, 3, 4, 5, 6, 12, 24, 36, 48, 60 or 72 months after transplantation.

Persistence may correlate with the efficacy of a therapeutic T cell transplant in the treatment of a disease, for example infection or cancer. The greater the persistence of the T cells, the more likely a therapeutic regime is to be effective, for example the less likely a tumour relapse will occur.

In some embodiments, the T cells persist in a recipient for at least 1, 2, 3, 4, 5, 6, 12, 24, 36, 48 or 72 months longer than T cells that have not been contacted with an agent or combination according to the invention.

In other embodiments, the T cells persist in a recipient in a form expressing CD62L for at least 1, 2, 3, 4, 5, 6, 12, 24, 36, 48 or 72 months longer than T cells that have not been contacted with an agent or combination according to the invention.

In some embodiments, the uses and methods of the invention increase T cell levels in a subject, in particular increase the fraction of total T cells in a subject (e.g. in the blood and/or spleen of a subject) that are transplanted cells and their descendants.

T cell function, levels and persistence may be assessed using methods for quantifying cells in vitro and in vivo that are known in the art. For example, transplanted cells may be genetically engineered to express a marker, for example a reporter protein (e.g. GFP or a surface tag) or DNA sequence, which can be detected ex vivo and used to quantify the numbers of the transplanted cells and their descendants. Cells may be analysed directly from peripheral blood or samples may be extracted from relevant tissues (e.g. bone marrow, lymph nodes and/or spleen). Analysis may be carried out in vitro using methods that are known in the art, for example by flow cytometry or by polymerase chain reaction.

Cell numbers and/or percentages in certain states (e.g. expressing certain markers, live, dead or apoptotic cells) may be quantified using any of a number of methods known in the art, including use of haemocytometers, automated cell counters, flow cytometers and fluorescence activated cell sorting machines. Markers may be identified by, for example, staining with antibodies specific for the marker. These techniques may enable distinguishing between live, dead and/or apoptotic cells.

Agent

When contacted with an in vitro culture of T cells, the agents of the invention may be used in any form suitable for in vitro cell culture (e.g. a non-toxic form). When administered to a subject, the agents of the invention may be used in any form suitable for ingestion by animals, preferably humans (e.g. are non-toxic).

The agents may be used, for example in compositions such as nutritional compositions, in any appropriate amount. The skilled person will be able to determine appropriate amounts depending on the desired dosage of the agent. Dosages may depend on factors such as the age, size and health status of the subject to whom they are administered, on lifestyle, as well as on genetic heritage. Dosages may be in line with the recommended daily intakes (RDA) developed by organisations such as the Food and Nutrition Board of the National Academy of Sciences.

Nicotinamide Riboside

Nicotinamide riboside (NR) is a pyridine-nucleoside form of vitamin B3, which is a precursor to nicotinamide adenine dinucleotide (NAD).

Nicotinamide riboside has the structure:

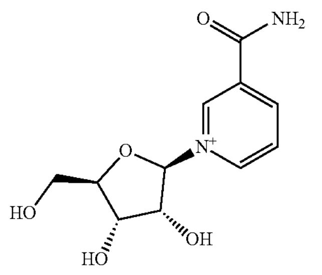 [SMILES: NC(=O)c1ccc[n+]([C@@H]2O[C@H](CO)[C@@H](O)[C@H]2O)c1]

In some embodiments, the T cells are contacted with the NR at a NR concentration of 1-10, 1-5, 1-2.5 or 1-2 mM. In other embodiments, the T cells are contacted with the NR at a NR concentration of 1, 2, 3, 4, 5, 6, 7, 8, 9 or 10 mM, preferably 2 mM.

Vitamin B12

Vitamin B12 (also known as cobalamine) is a class of cobalt-containing hydrosoluble vitamins which cannot be synthesised by the human body and must therefore be acquired from food or synthesised by the gut microbiota.

The vitamin B12 pool in the human body is composed of several forms: cyanocobalamin, which is inactive and requires conversion for activity, and methylcobalamin and adenosylcobalamin, which are the metabolically active forms of vitamin B12.

Two enzymes are known to rely on vitamin B12 as a cofactor: methionine synthase and methylmalonylCoA mutase. Methionine synthase is a cytoplasmic enzyme relying on methyl-cobalamine to convert homocysteine to methionine. It thereby plays a critical role in providing S-adenosylmethionine (SAM) as a methylation donor and preventing the toxic accumulation of homocysteine. Low SAM levels and high homocysteine levels observed upon severe vitamin B12 deficiency impair myelination of peripheral nerves and the spinal cord. Methionine synthase also catalyses the activation of 5-methyl-tetrahydrofolate into the bioactive tetrahydrofolate, which is required for 1-carbon metabolism and DNA synthesis, and thus for efficient red blood cell proliferation. MethylmalonylCoA mutase is a mitochondrial enzyme relying on adenosyl-cobalamine to convert methyl-malonylCoA to succinylCoA, which subsequently enters the TCA cycle. It is implicated in the degradation of branched-chain amino acids and odd-chain length fatty acids, and is essential during embryonic life to control neurological development, but is not vital in adult life The vitamin B12 of the invention may be in the form of, for example, vitamin B12 itself, the semi-synthetic derivative cyanocobalamin, hydroxocobalamin, methylcobalamin and/or adenosylcobalamin. Methylcobalamin may be particularly effective.

In some embodiments, the T cells are contacted with the vitamin B12 at a vitamin B12 concentration of 10-100 μM, 10-75 μM or 10-50 μM. In other embodiments, the T cells are contacted with the vitamin B12 at a vitamin B12 concentration of 25-100 μM, 25-75 μM or 25-50 μM. In other embodiments, the T cells are contacted with the vitamin B12 at a vitamin B12 concentration of 1, 2, 3, 4, 5, 6, 7, 8, 9, 10, 15, 20, 25, 30, 35, 40, 45, 50, 55, 60, 65, 70, 75, 80, 85, 90, 95 or 100 μM, preferably 50 μM.

In some embodiments, the vitamin B12 is administered to a subject at 0.1 to 40 times the recommended daily requirement (RDA) of Vitamin B12 per day, e.g. 1 to 10 times the recommended daily requirement (RDA) of Vitamin B12 per day.

The Vitamin B12 may thus be administered in a daily dose of about 10, 20, 30 or 40 times the RDA of the Vitamin B12 per day. Preferably, the daily dose provides 10 to 40, more preferably 10 to 30 or even more preferably 10 to 25 times the RDA of the Vitamin B12 per day, most preferably about 12 to 21 times the RDA of the Vitamin B12 per day.

The United States RDA of Vitamin B12 is 2.4 micrograms daily for humans of age 14 years and older, so such individuals may be administered a daily dose that provides about 0.002 mg to about 0.4 mg of Vitamin B12 per day, preferably 0.02 mg to 0.07 mg of Vitamin B12 per day, more preferably 0.03 mg to 0.05 mg of Vitamin B12 per day.

Urolithins

Urolithins are metabolites of dietary ellagic acid derivatives, such as ellagitannins, and are produced in the human gut by gut bacteria.

Example urolithins include urolithin A (3,8-dihydroxyurolithin), urolithin B (3-hydroxyurolithin), and urolithin D (3,4,8,9-tetrahydroxyurolithin), urolithin A glucuronide and urolithin B glucuronide.

Urolithin A (UroA) has the structure:

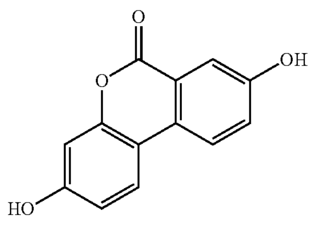 [SMILES: O=c1oc2cc(O)ccc2c2ccc(O)cc12]

In some embodiments, the T cells are contacted with the urolithin at a urolithin concentration of 1-20 μM, 1-15 μM or 1-10 μM. In other embodiments, the T cells are contacted with the urolithin at a urolithin concentration of 1, 2, 3, 4, 5, 6, 7, 8, 9, 10, 15 or 20 μM, preferably 5 μM.

Manganese

The manganese may be, for example, comprised in any form suitable for ingestion by a subject, preferably a human subject. For example, manganese may be comprised in the form of manganese chloride, manganese gluconate, manganese sulfate, manganese ascorbate, manganese amino acid chelates, manganese aspartate, manganese picolinate, manganese fumarate, manganese malate, manganese succinate, manganese citrate or a mixture thereof. Manganese(II)chloride may be particularly effective.

In some embodiments, the T cells are contacted with the manganese at a manganese concentration of 10-100 nM, 10-75 nM or 10-50 nM. In other embodiments, the T cells are contacted with the manganese at a manganese concentration of 25-100 nM, 25-75 nM or 25-50 nM. In other embodiments, the T cells are contacted with the manganese at a manganese concentration of 1, 2, 3, 4, 5, 6, 7, 8, 9, 10, 15, 20, 25, 30, 35, 40, 45, 50, 55, 60, 65, 70, 75, 80, 85, 90, 95 or 100 nM, preferably 50 nM.

In some embodiments, the manganese is administered to a subject in a dose of about 1.8-11, 2-3 or 2.5-2.7 mg/day.

Serine, Glycine, Arginine and Asparagine

In some embodiments, the T cells are contacted with the serine at a serine concentration of 1-10, 1-5, 1-2.5 or 1-2 mM. In other embodiments, the T cells are contacted with the serine at a serine concentration of 1, 2, 3, 4, 5, 6, 7, 8, 9 or 10 mM, preferably 2 mM.

In some embodiments, the T cells are contacted with the glycine at a glycine concentration of 1-10, 1-5, 1-2.5 or 1-2 mM. In other embodiments, the T cells are contacted with the glycine at a glycine concentration of 1, 2, 3, 4, 5, 6, 7, 8, 9 or 10 mM, preferably 2 mM.

In some embodiments, the T cells are contacted with the arginine at an arginine concentration of 1-15, 1-10 or 1-5 mM. In other embodiments, the T cells are contacted with the arginine at an arginine concentration of 1, 2, 3, 4, 5, 6, 7, 8, 9 or 10 mM, preferably 4 mM.

In some embodiments, the T cells are contacted with the asparagine at an asparagine concentration of 1-15, 1-10 or 1-5 mM. In other embodiments, the T cells are contacted with the asparagine at an asparagine concentration of 1, 2, 3, 4, 5, 6, 7, 8, 9 or 10 mM, preferably 4 mM.

The agent of the invention can be present as a salt or ester, where appropriate, in particular a pharmaceutically-acceptable salt or ester.

Pharmaceutically-acceptable salts of the agents of the invention include suitable acid addition or base salts thereof, as appropriate. A review of suitable pharmaceutical salts may be found in Berge et al. (1977) J Pharm Sci 66: 1-19.

The invention also includes where appropriate all enantiomers and tautomers of the agents. The skilled person will recognise compounds that possess optical properties (e.g. one or more chiral carbon atoms) or tautomeric characteristics. The corresponding enantiomers and/or tautomers may be isolated/prepared by methods known in the art.

Particularly effective agents may be nicotinamide riboside, vitamin B12, a urolithin and manganese. A particularly effective combination of agents may be nicotinamide riboside, vitamin B12, a urolithin and manganese.

Pharmaceutical and Nutritional Compositions

In some embodiments, the agent or combination is in the form of a pharmaceutical composition.

The pharmaceutical composition may further comprise a pharmaceutically acceptable carrier, diluent or excipient.

In some embodiments, the T cells are in the form of a pharmaceutical composition.

The cells of the invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy product is preferably performed in compliance with FACT-JACIE International Standards for cellular therapy.

In some embodiments, the agent or combination is in the form of a nutritional composition.

In some embodiments, the agent or combination is in the form of a food product, food supplement, nutraceutical, food for special medical purpose (FSMP), nutritional supplement, dairy-based drink, low-volume liquid supplement or meal replacement beverage. In some embodiments, the composition is an infant formula.

In some embodiments, the agent or combination is in the form of a food additive or a medicament.

A food additive or a medicament may be in the form of tablets, capsules, pastilles or a liquid for example. Food additives or medicaments are preferably provided as sustained release formulations, allowing a constant supply of the agent or combination for prolonged times.

The composition may be selected from the group consisting of milk-powder based products; instant drinks; ready-to-drink formulations; nutritional powders; nutritional liquids; milk-based products, in particular yoghurts or ice cream; cereal products; beverages; water; coffee; cappuccino; malt drinks; chocolate flavoured drinks; culinary products; soups; tablets; and/or syrups.

The composition may further contain protective hydrocolloids (such as gums, proteins, modified starches), binders, film forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials.

Further, the composition may contain an organic or inorganic carrier material suitable for oral or enteral administration as well as vitamins, minerals trace elements and other micronutrients in accordance with the recommendations of government bodies such as the USRDA.

The composition of the invention may contain a protein source, a carbohydrate source and/or a lipid source.

Any suitable dietary protein may be used, for example animal proteins (such as milk proteins, meat proteins and egg proteins); vegetable proteins (such as soy protein, wheat protein, rice protein and pea protein); mixtures of free amino acids; or combinations thereof. Milk proteins such as casein and whey, and soy proteins are particularly preferred.

If the composition includes a fat source, the fat source preferably provides 5% to 40% of the energy of the formula; for example 20% to 30% of the energy. DHA may be added. A suitable fat profile may be obtained using a blend of canola oil, corn oil and high-oleic acid sunflower oil.

A source of carbohydrates may more preferably provide between 40% to 80% of the energy of the composition. Any suitable carbohydrate may be used, for example sucrose, lactose, glucose, fructose, corn syrup solids, maltodextrins and mixtures thereof.

Adoptive T Cell Transfer

The invention provides a population of T cells prepared according to a method of the invention for use in therapy.

The use may be as part of a T cell transplantation procedure.

In another aspect, the present invention provides a cell of the invention or a cell prepared by a method of the invention for use in adoptive T-cell transfer, optionally the adoptive T-cell transfer may be allogenic adoptive T-cell transfer, universal non-alloreactive T-cell transfer, or autologous adoptive T-cell transfer.

The agent or combination of the invention may be used as part of an adoptive T cell transfer regimen. For example, a population of T cells may be contacted in vitro with an agent or combination of the invention before transplantation of the population into a subject. For example, an agent or combination of the invention may be administered to a subject (e.g. as part of a nutritional intervention) before, during and/or after an adoptive T cell transfer.

Adoptive cell transfer may be allogenic or autologous.

By "autologous cell transfer" it is to be understood that the starting population of cells (e.g. which is then contacted with an agent or combination of the invention) is obtained from the same subject as that to which the T cell population is administered. Autologous transfer is advantageous as it avoids problems associated with immunological incompatibility and is available to subjects irrespective of the availability of a genetically matched donor.

By "allogeneic cell transfer" is to be understood that the starting population of cells (e.g. which is then contacted with an agent or combination of the invention) is obtained from a different subject as that to which the transduced cell population is administered. Preferably, the donor will be genetically matched to the subject to which the cells are administered to minimise the risk of immunological incompatibility. Alternatively, the donor may be mismatched and unrelated to the patient.

Method of Treatment

It is to be appreciated that all references herein to treatment include curative, palliative and prophylactic treatment. Treatment may also include arresting progression in the severity of a disease.

The treatment of mammals, particularly humans, is preferred. Both human and veterinary treatments are within the scope of the invention.

The agents, combinations and T cells of the invention may be used for the treatment of an infection, such as a bacterial or viral infection.

The agents, combinations and T cells of the invention may be used to treat chronic infections, including cytomegalovirus (CMV) infections, Epstein-Barr virus (EBV) infections, human immunodeficiency virus (HIV) infections, hepatitis B virus (HBV) infections or hepatitis C virus (HCV) infections.

The T cells of the invention may be capable of killing target cells, for example cancer cells. Thus, the agents, combinations and T cells of the invention may be used for the treatment of cancer.

The agents, combinations and T cells of the invention may be used for the control of pathogenic immune responses, for example in autoimmune diseases, allergies or graft-versus-host rejection.

The agents, combinations and T cells of the invention may be used for the prevention or treatment of cancer, for example bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The agents, combinations and T cells of the invention may be used to prevent or treat: cancers of the oral cavity and pharynx which include cancer of the tongue, mouth and pharynx; cancers of the digestive system which include oesophageal, gastric and colorectal cancers; cancers of the liver and biliary tree which include hepatocellular carcinomas and cholangiocarcinomas; cancers of the respiratory system which include bronchogenic cancers and cancers of the larynx; cancers of bone and joints which include osteosarcoma; cancers of the skin which include melanoma; breast cancer; cancers of the genital tract which include uterine, ovarian and cervical cancer in women, prostate and testicular cancer in men; cancers of the renal tract which include renal cell carcinoma and transitional cell carcinomas of the ureters or bladder; brain cancers which include gliomas, glioblastoma multiforme and medullobastomas; cancers of the endocrine system which include thyroid cancer, adrenal carcinoma and cancers associated with multiple endocrine neoplasm syndromes; lymphomas which include Hodgkin's lymphoma and non-Hodgkin lymphoma; Multiple Myeloma and plasmacytomas; leukaemias, both acute and chronic, myeloid or lymphoid; and cancers of other and unspecified sites including neuroblastoma.

Treatment with the T cells of the invention may help prevent the escape or release of tumour cells which often occurs with standard approaches.

Administration

Although the agents, combinations and T cells for use in the invention can be administered alone, they will generally be administered in admixture with a pharmaceutical carrier, excipient or diluent, particularly for human therapy.

In some embodiments, an agent of the invention is in a combined preparation for simultaneous, separate or sequential use with one or more other agents of the invention.

The term "combination", or terms "in combination", "used in combination with" or "combined preparation" as used herein may refer to the combined administration of two or more agents simultaneously, sequentially or separately.

The term "simultaneous" as used herein means that the agents are administered concurrently, i.e. at the same time.

The term "sequential" as used herein means that the agents are administered one after the other.

The term "separate" as used herein means that the agents are administered independently of each other but within a time interval that allows the agents to show a combined, preferably synergistic, effect. Thus, administration "separately" may permit one agent to be administered, for example, within 1 minute, 5 minutes or 10 minutes after the other.

Dosage

The skilled person can readily determine an appropriate dose of one of the agents of the invention to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

Subject

In some embodiments, a subject is a human or non-human animal.

Examples of non-human animals include vertebrates, for example mammals, such as non-human primates (particularly higher primates), dogs, rodents (e.g. mice, rats or guinea pigs), pigs and cats. The non-human animal may be a companion animal.

Preferably, the subject is a human.

In some embodiments the subject is an immunocompromised subject, for example a subject that has undergone chemotherapy and/or radiotherapy.

Methods of Expansion and Culture Media

In another aspect, the invention provides a method for expanding an isolated population of T cells comprising contacting the population of T cells with an agent selected from the group consisting of nicotinamide riboside, vitamin B12, a urolithin, manganese, serine, glycine, arginine, asparagine, and a combination of two or more thereof.

In some embodiments, the contacting comprises culturing the population in the presence of the agent.

In some embodiments, the method comprises the steps:

(a) providing a population of T cells;

(b) activating the population of T cells;

(c) expanding the population of T cells; and (d) contacting the population during step (a), (b) and/or (c) with an agent or combination of the invention.

Suitable conditions and media for the culture, activation and expansion of T cells are known in the art. For example, activation of T cells may be achieved by culturing in the presence of IL-2 and an antigen (e.g. a peptide antigen). For example, expansion of T cells may be achieved by culturing in the presence of IL-2 and IL-7.

In another aspect, the invention provides a T cell culture medium comprising an agent or combination of the invention.

Kit

In another aspect, the invention provides a kit comprising the agents, combinations and/or cells of the invention.

The cells may be provided in suitable containers.

The kit may also include instructions for use.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1 (In Vitro Studies)

Materials and Methods

Unless specified otherwise, cell media were supplemented with agents or combinations of agents at the following concentrations:

| Agent | Concentration |
|---|---|
| Urolithin A (UroA) | 5 μM |
| Nicotinamide riboside (NR) | 2 mM |
| Mn ($MnCl_2$) | 50 nM |
| Serine | 2 mM |
| Glycine | 2 mM |
| Vitamin B12 | 50 μM |
| Arginine | 4 mM |
| Asparagine | 4 mM |

| Agent combination | Respective concentrations |
|---|---|
| NR/UroA/Mn | 2 mM/5 μM/50 nM |
| NR/B12/Mn | 2 mM/50 μM/50 nM |
| UroA/B12/Mn | 5 μM/50 μM/50 nM |
| NR/UroA/B12 | 2 mM/5 μM/50 μM |
| Ser/Gly/$B12_{25\ \mu M}$ | 2 mM/2 mM/25 μM |
| Ser/Gly/$B12_{50\ \mu M}$ | 2 mM/2 mM/50 μM |

T Cell Preparation (Total Splenocytes)

An OTI-1 mouse was sacrifice and dissected to extract the spleen. Under sterile conditions, the spleen was disrupted over a 0.70 μm filter. PBS was then added to the disrupted spleen to a volume of 30 mL, and the mixture was centrifuged (1500 rpm, 5 min at room temperature).

The PBS supernatant was discarded and the cells resuspended in 2 mL of 1× red blood cell lysis buffer for 3 min. 15 mL of PBS was then added to wash the cells, and the mixture was centrifuged (1500 rpm, 5 min at room temperature).

The PBS supernatant was discarded and the cells resuspended in fresh RPMI completed media (+10% FBS, Sodium Pyruvate) before counting.

CD8+ T-Cell Stimulation (Day 0-Day 3)

750 μL of agent/agent combination supplementation solutions (described above) were added to corresponding wells of a flat bottom 24-well plate.

The total splenic cells were then resuspended in RPMI completed media (+10% FBS, Sodium Pyruvate), including IL-2 (final concentration 100 U/mL) and SIINFEKL peptide (final concentration 250 nM) at $1.6\times10^6$ cells/mL.

750 μL of cell solution (2×) were added to each well. Thus, the cell count was 1200000 cells per well at $0.8\times10^6$ cells/mL.

The cells were then incubated at 37° C. for 3 days.

The specific activation of OTI-1 T-cells is due to the SIINFEKL peptide. Therefore after 3 days, mostly (if not only) CD8 T-cells will have proliferated and show an activation profile.

CD8+ T-Cell Stimulation (Day 3-Day 7)

The cells from each condition (after day 3) were counted and resuspended in RPMI completed media (+10% FBS, Sodium Pyruvate) at $1.2\times10^6$ cells/mL.

The cells were then distributed in 96-well or 12-well plates at $5\times10^4$ cells/well (96-well plate) and $6\times10^6$ cells/well (12-well plate).

Agent/agent combination supplementation solutions (described above) or complete media were added to corresponding wells in addition to either: (a) IL-2 (at a final concentration of 100 U/mL) and IL-7 (at a final concentration of 10 U/mL) (to keep the effector phenotype); or (b) IL-15 (at a final concentration of 10 U/mL) (to induce differentiation into memory precursor effector cells (MPECs) as a positive control.

Extra media was added at day 5 to the wells with fresh agents and cytokines.

The cells were then incubated at 37° C. for 4 days before proceeding with FACS staining or Seahorse analysis.

FACS Analysis

Cells were harvest from the 96-well plates and centrifuged (2000 rpm, 2 min at 4° C.) before washing with 150 μL of PBS.

The cells were then resuspended in 60 μL of LiveDead dye solution (1:500 dilution in PBS) and incubated for 15 min on ice. Cells were then centrifuged (2000 rpm, 2 min at 4° C.) before washing with 150 μL of PBS and then 200 μL of FACS buffer (PBS+2% FBS).

Subsequently, the cells were resuspended in 60 μL of stain solution (FACS buffer+antibodies specific for CD45.1, CD62L and CD8), and incubated for 15 min on ice.

Cells were then centrifuged (2000 rpm, 2 min at 4° C.) before washing with 150 μL of FACS buffer, and then resuspended in 150 μL of FACS buffer before analysis by FACS (BD™ LSR II).

After acquisition, FACS data were analysed using the FlowJo treestar software and median fluorescence for CD62L was extracted.

Seahorse Analysis

Cells were harvested from 12-well or 6-well plates.

A probe plate containing cartridge pores (Seahorse XFe96 FluxPak) was prepared by adding 200 μL of Seahorse XF Calibrant solution (Agilent) to each well and incubating overnight at 37° C. (no $CO_2$).

Residues were removed by transferring the cells to a 15 mL tube and a Pasteur pipette was added. 2 mL of Lympholyte M was slowly added to the Pasteur pipette, and the Ficoll was allowed to slowly release below the cells before the pipette was removed from the tube. The tube was the centrifuged at 1500 rpm, 10 min at room temperature without braking.

5 mL of fresh uncompleted RPMI was added to the cells, and the mixture was centrifuged at 1500 rpm, 5 min at room temperature. The cells were then resuspended in 1 mL of RPMI completed media (+10% FBS, Sodium Pyruvate).

Subsequently, the cells were counted before being resuspended at $5\times10^6$ cells/mL in completed XF Medium (non-buffered RPMI, with glucose (25 mM), L-glutamine (2 mM) and sodium pyruvate (1 mM), pH 7.3).

40 μL of cells were then distributed in corresponding pre-determined Poly-D-Lysine coated wells of a cell culture plate (V3-PS TC-Treated) and the plate was centrifuged at 400 g, 5 min.

140 μL of XF Medium was carefully added to each well, and the plate was incubated at 37° C., 30-60 min (no $CO_2$). During this time modulator solutions (Oligomycin 10 μM; FCCP 15 μM; Rotenone/Antimycin A 1 μM/1 μg/mL) were loaded into the previously prepared cartridge pores: 20 μL of Oligomycin in pore A; 22 μL of FCCP in pore B; and 24 μL of Rotenone/Antimycin A in pore C) and the cartridge was incubated at 37° C. (no $CO_2$).

Mitochondrial stress analysis was then carried out using the Wave software following the manufacturer instructions.

After data acquisition, oxygen consumption rates were extracted and spare respiratory capacity calculated following the manufacturer's instructions.

Results and Discussion

To study the enhancement of T cell immune fitness the in vitro studies focused on the development of T cells with long term and resting phenotypes, which could be equated to the development of memory cell characteristics. The metabolic intervention outcomes were evaluated using:

- Cell phenotype: assessment by FACS of the cell surface expression of the specific marker CD62L, which is higher on resting T-cells.
- Cell function: assessment using metabolic potential measurement (as per the Spare Respiratory Capacity) by means of an assay assessing cell respiration upon mitochondrial stress (Seahorse technology), which is higher in memory, quiescent cells.

Metabolic interventions testing independently UroA, NR, Mn, Ser, Gly, vitamin B12, Arg and Asn each improved T cell phenotype and function, as defined by a higher level of CD62L surface expression and a higher metabolic potential than the negative control (effector T cells expanded with IL-2/7).

NR and B12 displayed similar or higher CD62L expression level than the positive control (memory T cells differentiated using IL-15), further demonstrating their enhancing effect on T-cell immune fitness (FIG. 1A).

Metabolic interventions testing the agent combinations Ser/Gly/$B12_{25\ \mu M}$, Ser/Gly/$B12_{50\ \mu M}$, NR/UroA/Mn, NR/B12/Mn, UroA/B12/Mn and NR/UroA/B12 each improved T cell phenotype, as defined by a higher level of CD62L expression at the cell surface than the negative control. In addition, the combinations Ser/Gly/$B12_{25\ \mu M}$, Ser/Gly/$B12_{50\ \mu M}$, NR/UroA/Mn, NR/B12/Mn and NR/UroA/B12 improved T cell function, as defined by a higher metabolic potential than the negative control (FIGS. 1B and 1C).

All combinations displayed similar or higher CD62L expression level than the positive control, and NR/UroA/Mn, NR/B12/Mn and NR/UroA/B12 showed higher metabolic potential (approximately 2-fold) to the positive control (IL-15 ™), further demonstrating their enhancing effect on T cell immune fitness (FIGS. 1B and 1C).

Importantly, these results showed that Ser/Gly/$B12_{25\ \mu M}$, Ser/Gly/$B12_{50\ \mu M}$, NR/UroA/Mn, NR/B12/Mn and NR/UroA/B12 combinations have a synergetic effect on the metabolic potential (FIGS. 1B and 1C).

Example 2 (In Vivo Studies)

Materials and Methods

The metabolic intervention consisted of cell medium supplementation as described above for the in vitro procedure) using the following agent concentrations, before adoptive transfer of the cells into infected mice.

| Agent | Concentration |
|---|---|
| Urolithin A (UroA) | 5 μM |
| Nicotinamide riboside (NR) | 2 mM |
| Vitamin B12 | 50 μM |
| Arginine | 4 mM |

For the in vivo assessment, the positive control was obtained by pre-treating the OTI-1 CD8 T-cells in vitro with Phenformin (100 μM) following the same procedure as for the other agents). Phenformin is known to induce a metabolic switch in cells essential for the development of long-term T-cells.

Adoptive Transfer and *Listeria monocytogenes* Infection

C57BL/6 mice were injected intravenously with 2000 CFU of *Listeria monocytogenes* bacteria expressing OVA at a concentration of $1\times10^4$ CFU/mL (Lm-OVA; harvested in Brain Heart Infusion media without antibiotics until OD reached 0.3) in 200 μL of PBS to induce a *Listeria monocytogenes* infection.

Treated OTI-1 T-cells (specific for OVA recognition) were provided from day 7 of the procedure described above in Example 1 at a concentration of $1\times10^5$ cells/mL in PBS. Residues were cleaned from the T cells using Lympholyte M as described above.

Adoptive transfer of OTI-1 T cells was carried out by intravenously injecting each mouse with $1\times10^4$ cells in 200 μL of PBS.

After 35 days, the mice were sacrificed to collect blood and spleens for further surface and intracellular FACs analysis.

Surface FACS Analysis

Harvested blood or total spleen cells were subjected to red blood cell lysis in a 96-well plate and then centrifuged (2000 rpm, 2 min at 4° C.) before washing with 150 μL of PBS.

The cells were then resuspended in 60 μL of LiveDead dye solution (1:500 dilution in PBS) and incubated for 15 min on ice. Cells were then centrifuged (2000 rpm, 2 min at 4° C.) before washing with 150 μL of PBS and then 200 μL of FACS buffer (PBS+2% FBS).

Subsequently, the cells were resuspended in 60 μL of stain solution (FACS buffer+antibodies specific for CD45.1, CD62L, CD8, CD127, KLRG1, CD27, CD43 and CXCR3), and incubated for 15 min on ice.

Cells were then centrifuged (2000 rpm, 2 min at 4° C.) before washing with 150 μL of FACS buffer, and then resuspended in 150 μL of FACS buffer before analysis by FACS (BD™ LSR II).

After acquisition, FACS data were analysed using the FlowJo treestar software and percentages of gated cells for targeted markers were extracted.

Intracellular FACS Staining

Harvested blood or total spleen cells were subjected to red blood cell lysis in a 96-well plate and then centrifuged (2000 rpm, 2 min at 4° C.) before the supernatant was discarded.

Optionally, 50 μL of 24G2 supernatant (culture supernatant from rat cell line 24G2, diluted 1:1 with FACS buffer (PBS+2% FBS)) was added to each well and incubated for 15 min at 4° C. to block the Fc receptor on cells, preventing unspecific antibody binding.

The cells were then centrifuged (2000 rpm, 2 min at 4° C.) before washing with 100 μL of PBS.

The cells were then resuspended in 60 μL of LiveDead dye solution (1:500 dilution in PBS) and incubated for 15 min at 4° C. Cells were then centrifuged (2000 rpm, 2 min at 4° C.) before washing with 100 μL of FACS buffer.

The cells were then centrifuged (2000 rpm, 2 min at 4° C.) and resuspended in surface antibody mix (antibodies specific for CD45.1, CD8; 50 μL in FACS Buffer) before incubating for 15 min at 4° C.

Subsequently, the cells were centrifuged (2000 rpm, 2 min at 4° C.) and washed with 100 μL of FACS buffer.

150 μL of the 1× Fixation/Permeabilization buffer (Intracellular staining kit (BD™)) was added and incubated for 30 min or overnight.

The cells were then centrifuged (2000 rpm, 2 min at 4° C.) and the supernatant was discarded.

The cells were then washed with 200 μL of 1× Permeabilization buffer (Intracellular staining kit (BD™)) before centrifuging (2000 rpm, 2 min at 4° C.) and discarding the supernatant.

Intracellular staining was then carried out by adding 50 μL of 1× Permeabilization buffer (Intracellular staining kit (BD™)) and antibodies (specific for IFNγ and TNFα). The mixture was incubated for 30 min at 4° C.

The cells were the centrifuged (2000 rpm, 2 min at 4° C.) and washed with 150 μL of 1× Permeabilization buffer (Intracellular staining kit (BD™)), and then centrifuged (2000 rpm, 2 min at 4° C.) and washed with 200 μL of FACS buffer. 200 μL of FACS buffer was then added and the mixture stored at 4° C. till analysis by FACS (BD™ LSR II) either the same or following day.

After acquisition, data were analysed using the FlowJo treestar software and percentages of gated cells for the targeted markers were extracted.

Results and Discussion

To study the enhancement of T cell immune fitness the in vivo studies focused on the development of T cells with long term and resting phenotypes after treatment and adoptive transfer into mice simultaneously infected with *Listeria monocytogenes*. The metabolic intervention outcomes were evaluated after 35 days of infection using:

- Cell frequency: assessment by FACS of the percentage of transferred cells (CD45.1) from total CD8 positive T cells in the mice blood and spleen.
- Cell phenotype: assessment by FACS of the percentage of cells from the blood and spleen that developed memory patterns from total CD8 positive transferred cells (CD45.1): either memory precursor effector cells (MPECs; both positive for CD127 and negative for KLRG1 markers) or full memory cells (positive for both CD27 and CD43 markers).
- Cell function: assessment by FACS of the percentage of transferred cells (CD45.1) from total CD8 positive T cells in the mice spleen expressing the functional surface marker CXCR3 and able to produce both IFNγ and TNFα cytokines by intracellular staining.

Figure 2:
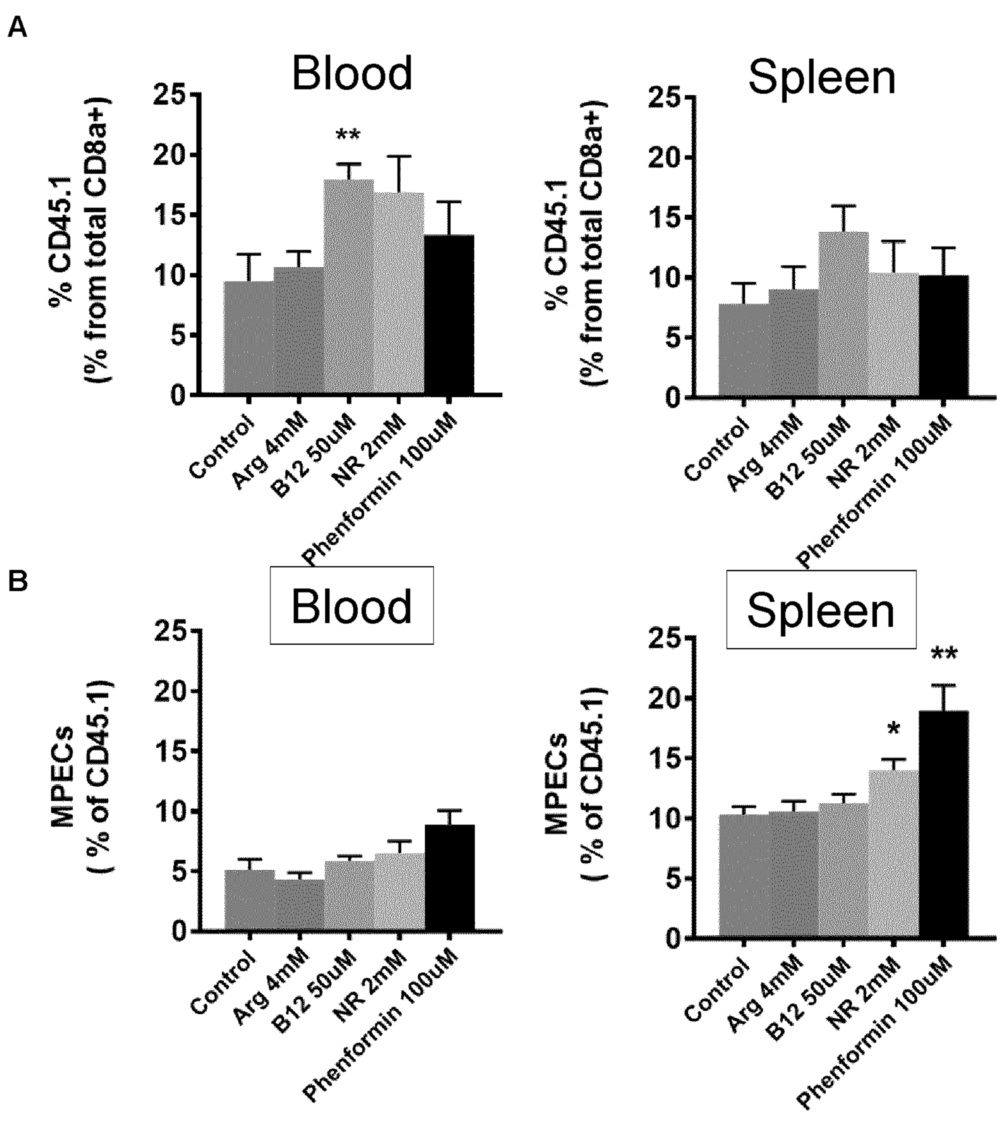
Figure 2:
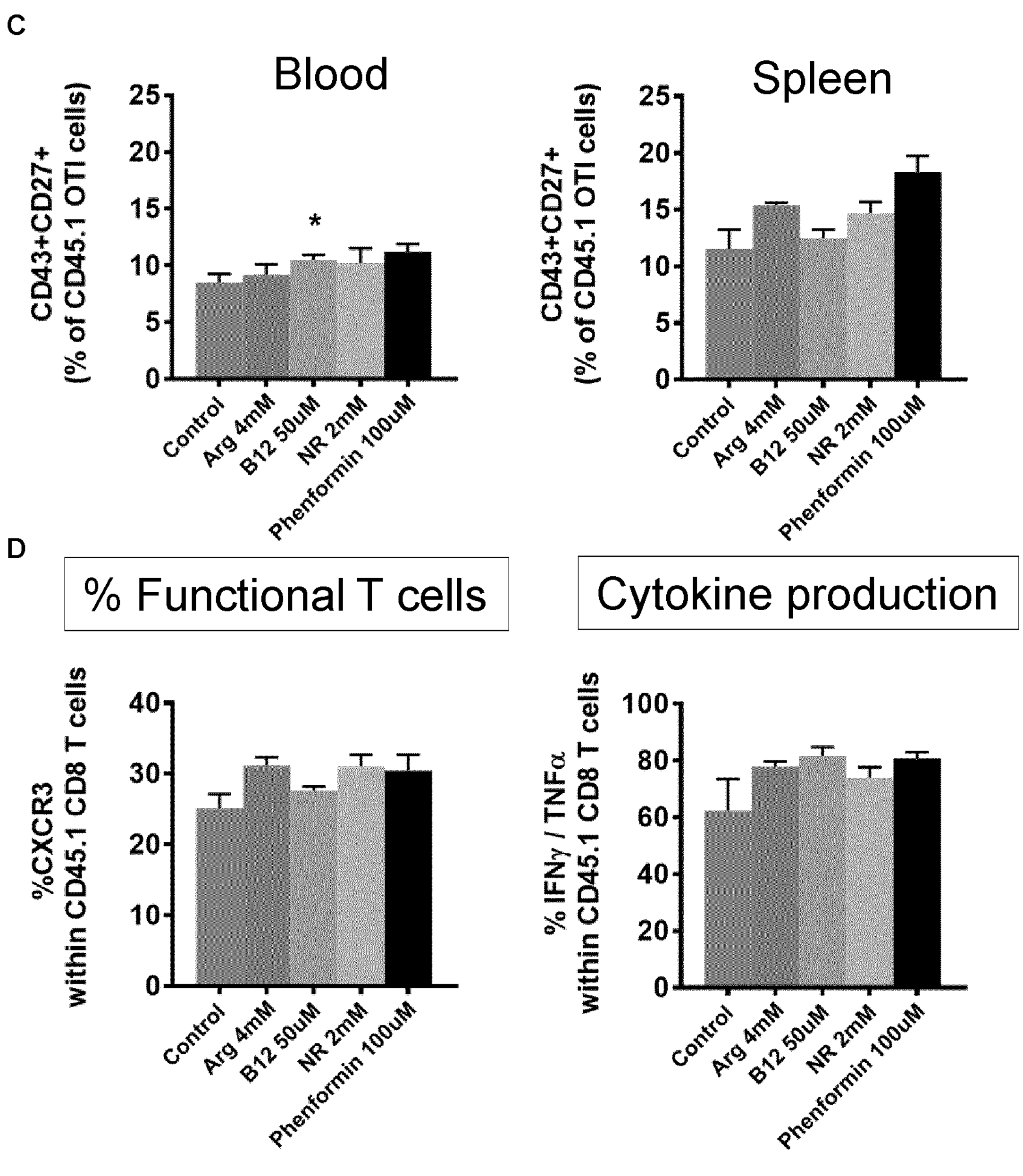

Metabolic interventions testing independently Arg, NR and B12 improved T cell immune fitness, as defined by a higher level of cell frequency in the blood and spleen than the control (FIG. 2).

In addition, Arg, NR and B12 improved T cell phenotype, as defined by a higher percentage of MPECs (B12 notably in the spleen; NR in both blood and spleen) and/or memory cells (Arg in the spleen; B12 and NR in both blood and spleen) (FIG. 2). Importantly, the observed effects for all compounds are concomitant with similar or improved cell function, as defined by a higher percentage of cells expressing CXCR3 and producing both IFNγ and TNFα cytokines (FIG. 2).

Notably, B12 displayed higher frequency levels of transferred cells in both blood and spleen than the positive control (Phenformin treatment). In addition, NR displayed higher (blood) or similar (spleen) frequency levels of transferred cells than the positive control (Phenformin treatment). These results further demonstrated the enhancing effect on T cell immune fitness (FIG. 2).

All publications mentioned in the above specification are herein incorporated by reference. Various modifications and variations of the disclosed agents, compositions, uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A method for treatment of (a) a bacterial or viral infection or (b) cancer that is at least one of a lymphoma, multiple myeloma or a leukaemia, the method comprising administering an effective amount of a composition comprising a) nicotinamide riboside, a urolithin and manganese; (b) nicotinamide riboside, vitamin B12 and manganese; (c) nicotinamide riboside, a urolithin and vitamin B12; or (d) nicotinamide riboside, vitamin B12, a urolithin and manganese to a subject in need of the treatment.

2. The method according to claim 1, wherein the composition further comprises at least one pharmaceutical carrier, diluent or excipient.

3. The method according to claim 1, wherein the composition comprises a combination of nicotinamide riboside, vitamin B12, a urolithin, and manganese.

4. The method according to claim 1, wherein the composition comprises a) nicotinamide riboside, a urolithin A and manganese; (b) nicotinamide riboside, vitamin B12 and manganese; (c) nicotinamide riboside, urolithin A and vitamin B12; or (d) nicotinamide riboside, vitamin B12, urolithin A and manganese.

5. The method according to claim 1, wherein the composition is a pharmaceutical or nutritional composition.

6. The method according to claim 1, wherein the composition is a food product, food supplement, nutraceutical, food for special medical purpose (FSMP), nutritional supplement, dairy-based drink, liquid supplement, or meal replacement beverage.

7. The method according to claim 1, wherein the subject in need of the treatment is an immunocompromised subject.

8. The method according to claim 1, wherein the subject in need of the treatment has undergone at least one intervention selected from the group consisting of chemotherapy, radiotherapy and surgery.

9. The method of claim 1, wherein the composition further comprises one or more of serine, glycine, arginine, and asparagine.

10. The method of claim 1, wherein the composition is administered as a sustained release formulation.

* * * * *